United States Patent [19]

Brace et al.

[11] Patent Number: 4,932,255
[45] Date of Patent: Jun. 12, 1990

[54] FLOW SENSING USING SURFACE ACOUSTIC WAVES

[75] Inventors: John G. Brace, Brown Deer; Thomas S. Sanfelippo, Milwaukee, both of Wis.

[73] Assignee: Johnson Service Company, Milwaukee, Wis.

[21] Appl. No.: 285,625

[22] Filed: Dec. 16, 1988

[51] Int. Cl.⁵ .................. G01F 1/68; G01N 30/00
[52] U.S. Cl. ..................... 73/204.11; 73/DIG. 4; 73/24.03; 310/313 R
[58] Field of Search ........... 73/23, 204.11, 204.14, 73/204.17, DIG. 4; 310/313 R, 313 D; 333/155, 151

[56] References Cited

U.S. PATENT DOCUMENTS

| | | | |
|---|---|---|---|
| 4,055,072 | 10/1977 | Fletcher | 73/23 |
| 4,090,153 | 5/1978 | Toda et al. | 310/313 R X |
| 4,312,228 | 1/1982 | Wohltjen | 73/23 X |
| 4,361,026 | 11/1982 | Muller et al. | 73/23 |
| 4,510,410 | 4/1985 | Yuhara et al. | |
| 4,604,594 | 8/1986 | Angerer et al. | |
| 4,726,225 | 2/1988 | Brace et al. | |

OTHER PUBLICATIONS

Anderson, A. C. et al.–Attenuating Thin Films For SAW Devices, Proceedings 1980 Ultrasonics Symposium, pp. 442–443, 1980 IEEE.
N. Ahmad–Surface Acoustic Wave Flow Sensor, Proceedings IEEE 1985 Ultrasonics Symposium.
Martin, S. J. et al.–Isothermal Measurement and Thermal Desorption using SAW Devices, Technical Digest 1986, IEEE Solid State Sensors Workshop.

Primary Examiner—Charles A. Ruehl
Attorney, Agent, or Firm—Foley & Lardner

[57] ABSTRACT

A sensor employs a SAW oscillator heated above the ambient by converting RF energy to heat via acoustic dissipation in energy absorbers located outside the path of propagation. The oscillator utilizes a delay line designed to support single mode operation, fabricated on a substrate. Low insertion loss results from placing the energy absorbers outside the propagation path. Thermally conductive paths around the substrate periphery reduce thermal gradients. Used to measure fluid flow, fluid is directed across the SAW delay line lowering the substrate temperature which is elevated by the heat generating energy absorbers outside the propagation path. The temperature reduction changes the oscillator frequency, indicative of the gas velocity. In operation, gases are passed across the top of the delay-line while liquids are passed across the bottom of the delay-line in a back-side sensing operation. To measure gas or vapor contaminants, chemically sensitive coatings placed on the substrate in the propagation path can be used to sense contaminants in a gas flowing over the substrate. In mass flow sensing applications a difference frequency between an oscillator with a delay-line having end absorbers and operating at elevated temperatures and a reference oscillator with a delay-line operating at ambient is determined.

19 Claims, 4 Drawing Sheets

FLOW SENSING USING SURFACE ACOUSTIC WAVES

INTRODUCTION

1. Field of the Invention

The invention relates generally to sensors and more particularly to a surface acoustic wave delay line sensor.

2. Related Art

Commonly owned U.S. Pat. No. 4,726,225 discloses a Surface Acoustic Wave Gas Flow Rate Sensor With Self-Heating Feature and is incorporated herein by reference. The self heating SAW delay line sensor taught by this patent employs an energy absorbing medium in the propagation region between transmitting and receiving interdigital transducers. The energy absorbed by the medium generates heat and increases the temperature of the propagation region over that of the surrounding ambient. Gas flow across the sensor decreases the temperature. This temperature decrease results in an increase in resonant frequency which is measured and converted to flow rate. The sensitivity of the flow sensor increases with the quiescent temperature. The quiescent temperature is a function of the power dissipated in the absorber in the propagation region. However, power dissipation in the energy absorbing coating in the propagation region increases insertion loss of the delay line.

A. C. Anderson, V. S. Dolat and W. T. Brogan in "Attenuating Thin Films For SAW Devices," *Proceedings 1980 Ultrasonics Symposium*, pp. 442-3, describe the effects of resistive films deposited on SAW devices. Anderson shows strips of cermet films photolithographically patterned in the path of a delay line of known insertion loss, describes the expected effect of a resistive film on attenuation and phase shift of a SAW and shows data on the added attenuation. Anderson also discloses a reflection array compressor (RAC), which does not appear to be a delay line. This signal processing structure has resistive attenuating films at the ends to reduce spurious noise generation. Nothing in Anderson suggests that resistive attenuating films at the ends are useful for generating heat that can be used in sensor applications.

U.S. Pat. No. 4,604,594 to Angerer et al discloses a Surface Wave Filter Having Photoresist Damping Material Thereon And a Method For Manufacturing The Same. An organic photoresist is placed around the periphery of a SAW device to provide reflection damping. Since such organic photoresists are not good thermal conductors, they are not performed in sensor applications requiring heat generation. Angerer discloses neither a sensor nor a delay line but rather a filter incorporating a multistrip coupler (MSC) which increases spurious reflections. Moreover, Angerer does not teach heat generation or utilization.

U.S. Pat. No. 4,510,410 assigned to Hitachi teaches Elastic Surface Wave Absorbers Comprising Ultraviolet Light Curable Resin. This patent deals with acoustic impedances and viscoelastic properties of absorber materials in the context of acoustic energy dissipation at the edges of $LiNbO_3$ SAW delay lines. No mention is made of SAW delay line sensor applications or the utilization of heat created in the absorbers.

N. Ahmad in "Surface Acoustic Wave Flow Sensor", *Proceedings IEEE 1985 Ultrasonics Symposium*, discloses a SAW flow sensor with a separate resistive film heater. Similarly, S. J. Martin, A. J. Ricco and T. E. Zipperian in "Isothermal Measurement and Thermal Desorption Using SAW Devices, *Technical Digest*, 1986 *IEEE Solid-State Sensors Workshop*, disclose a chemical sensor using a separate heater in the SAW propagation path to purge or desorb compounds present on the SAW sensor. There is no disclosure in either document of a sensor employing self heating effects.

SUMMARY OF THE INVENTION

It has been determined that, since interdigital transducers are bidirectional, acoustic power generated by one of the transducers will be incident on absorbers outside the direct propagation path between the transducers. Thus, a surface acoustic wave delay line sensor has interdigital transmitting and receiving transducers mounted on the surface of a substrate and acoustic end absorbers located outside the propagation region between each interdigital transducer and the corresponding end of the substrate. The transducers are configured to have operating frequencies between 10 MHz and 1000 MHz and to support a single mode of oscillation. The SAW delay line is formed on a piezoelectric substrate having a temperature coefficient of delay on the order of $10^{-4}/°C$. The propagation region on the substrate surface between the transducers has no energy absorbers. The acoustic end absorbers act to absorb primarily mechanical energy to provide efficient self-heating needed for measuring the velocity of a fluid passing across the SAW delay line. In one embodiment of the invention gases are passed across the top surface of the substrate, while in another embodiment of the invention, liquids are passed across the back side of the substrate.

In another embodiment, a thermally conductive material is placed on the periphery of the substrate to evenly distribute heat on the delay line and reduce the thermal gradient across the device.

The absence of energy absorbers in the propagation region reduces insertion loss and therefore increases sensitivity. The acoustic end absorbers are also less sensitive to changes in ambient conditions such as humidity than absorbers located in the propagation path.

In another embodiment, a coating is provided in the propagation region to provide sensitivity to contaminants in a gas flowing over the SAW delay line.

It is therefore an object of the invention to make use of energy outside the propagation path to provide the useful function of self-heating.

It is a further object of the invention to reduce insertion loss of an SAW delay line sensor.

It is another object of the invention to reduce sensitivity to extraneous ambient conditions.

It is a further object of the invention to evenly distribute the heat generated by the end absorbers on the delay line.

It is a further object of the invention to provide an SAW device for measuring a velocity of gas passing over the delay line.

DETAILED DESCRIPTION OF THE PREFERRED EMBODIMENTS

Figure 1:
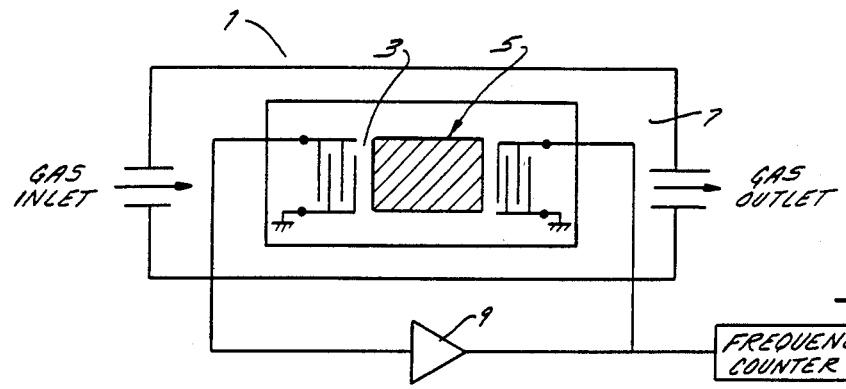
FIG. 1 is a schematic diagram of a self-heating SAW oscillator gas-flow sensor with a propagation-path absorber previously discussed.

A self-heating SAW flow sensor is shown in FIG. 1. It consists of a SAW delay-line oscillator 1 in which a part of the propagation path 3 is coated with an acoustically lossy material 5. Dissipation of acoustical energy in this material causes heating of the substrate 7. When such a delay line is connected in the feedback loop of an RF amplifier 9 having sufficient power output, not only is stable oscillation obtained, but surface temperature increases rapidly above ambient upon commencement of oscillation.

Depending upon the thermal conductivity of the substrate 7, its thermal mass and the magnitude of all parasitic thermal paths, the quiescent substrate temperature eventually achieves steady state at a value $\theta$. This temperature is a function of RF power in the oscillator loop. When a flowing fluid is passed across the delay line, the substrate temperature will decrease due to forced convective heat transport. The reduction in $\theta$ changes the frequency of the SAW oscillator. With a high negative temperature coefficient material such as LiNbO$_3$, the oscillator frequency increases with increased fluid flow rate.

Figure 2:
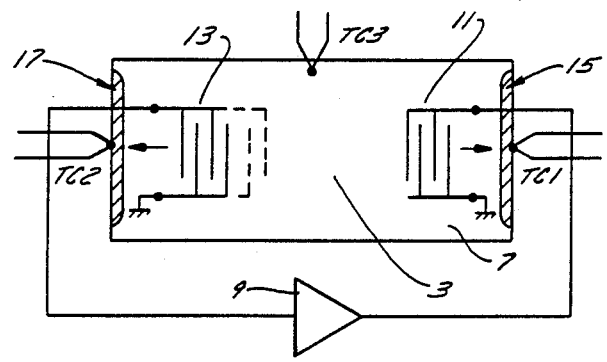
FIG. 2 is a schematic of a self-heating SAW oscillator with end absorbers.
Figure 3A:
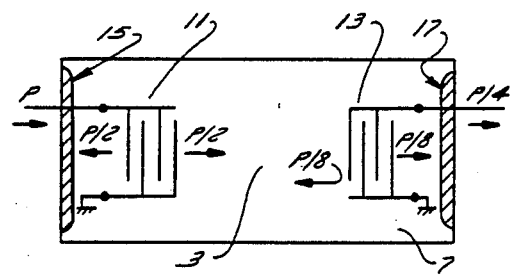
FIG. 3(a) illustrates distribution of acoustic power in a SAW delay line. RF power is supplied to transducer $T_1$.

A new sensor structure with acoustic absorbers placed outside rather than in the direct propagation path is as shown in FIG. 2. Since the interdigitated transducers 11, 13 (IDT's) are bidirectional, acoustic power generated at IDT 11 will propagate both left and right with approximately equal power. Thus, acoustic power from IDT 11 will be incident on absorbers 15 and 17 even though they lie outside the direct path between the input and output transducers. The distribution of power in the device of FIG. 2 is shown in FIG. 3(a).

A bidirectional collimated acoustical beam of width W (the overlap distance of the IDT fingers) is generated at the input IDT by applying RF power. If P is the total power supplied to transducer 11, P/2 is incident on absorber 15 and slightly less than P/2 is incident on the transducer 13. Approximately half this power or P/4 is transduced to RF voltage appearing across the output of the IDT. P/8 is reflected and the remaining fraction P/8 is incident on the absorber 17 beyond the IDT to be dissipated as heat. Thus, if P is the power supplied to transducer 11, then the fractions P/2 and P/8 will be incident on absorbers 15 and 17 respectively. Neglecting the power carried by triple transit and subsequent signals and assuming the IDTs 11 and 13 are tuned and matched, a total power of 5P/8, which is P/2+P/8, is available for heating the device. It is thus unnecessary to provide energy absorbing material in the propagation region to achieve self heat.

The use of end absorbers as shown in FIG. 2 has several advantages over the propagation path absorber of FIG. 1. In flow sensing applications the sensitivity of the flow sensor increases with the quiescent substrate temperature $\theta$. This temperature in turn depends on the power dissipated in the absorbers 15, 17. However, the added mass or charge carriers in the propagation path absorber 5 increases the insertion loss of the delay line when power is dissipated in the propagation path absorber 5. Thus, there is a conflict between the requirements of large power dissipation in the absorber and low insertion loss. When absorbers lie outside the direct propagation path 3, attenuation in the absorbers 15, 17 does not increase the delay line's insertion loss. Thus, the arrangement of FIG. 2 uses power that would normally have been wasted to perform a new and useful function, namely that of heating the substrate. In addition, any changes in the properties of the propagation path absorber 5 due to changes in humidity, gas concentration or composition can have an appreciable effect on the sensing response of the device. These factors have negligible impact on the device of FIG. 2, which uses end absorbers 15, 17.

The absorber material may be chosen from several categories that provide various capabilities for self-heating. The primary criterion for self-heating is that the absorber absorb energy from the substrate surface, i.e., from the mechanical components of the impinging Rayleigh wave or from the electric field associated with this wave and due to the piezoelectricity of the substrate. Thus, the absorber material may be a viscous liquid or a solid, and electrically conductive, semiconductive or insulative. Although the absorber material may be thermally conductive or insulative, a preferred class of materials is those that are thermally conductive. Other suitable classes are rubbery polymers, composite microwave absorbers, conductive paints and inks. A highly preferred class of materials is thermally conductive epoxies, which contain thermally conductive particles in an epoxy matrix. The absorber thickness is not critical, since complete attenuation of the SAW is desirable. Thickness may range from much less than one to many acoustic wavelengths.

Experiments have been carried out using 75 MHz SAW delay lines fabricated on 0.5 mm thick, 128°-rotated-Y-cut, X-propagating LiNbO$_3$ substrate. Typically, the delay line had interdigital transducers 11 and 13 with ten and thirty finger pairs, respectively. The IDT's had a periodicity, p, of 52.5 $\mu$m and an aperture, W, of 2800 $\mu$m. In order to support a single mode of oscillation, the spacing between transducers was set at 30 p or 1575 $\mu$m. The substrate size was, for most experiments, 5 mm × 7 mm × 0.5 mm. The absorbers consisted of a thin layer of thermally conductive but electrically insulative epoxy applied at each end of the delay line. With or without absorbers, the untuned, unmatched insertion loss of the delay line in a 50Ω system was 8.0 dB and was independent of applied RF power. The temperature at various points on the substrate was monitored, using miniature thermocouples TC$_1$, TC$_2$ and TC$_3$ as shown in FIG. 2. The SAW device was mounted to either a polycarbonate plate or TO-8 header (not shown) with silicone-rubber sealant so that it was fairly well thermally isolated from its mount. An air-tight test cell, also of polycarbonate construction, was provided with inlet and outlet for gas flow. The sensor orientation and cell aperture were varied in order to achieve specific flow conditions at the sensor surface. A broadband RF amplifier 9 having maximum gain of 24 dB and power output of 1 W, and a 0–12 dB variable attenuator (not shown), completed the SAW oscillator loop. The RF power fed to the input transducer could be varied either by the attenuator setting or by varying the d.c. supply voltage to the amplifier, since this effectively varied the amplifier gain.

Figure 3B:
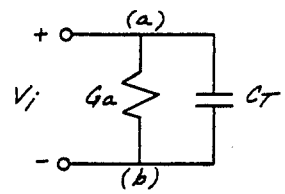
FIG. 3(b) is an equivalent circuit valid for $T_1$ at the resonant frequency.

The acoustic power dissipated in absorbers 15 and 17 can be calculated from the equivalent-circuit parameters of input transducer 11. The shunt-equivalent circuit of IDT 11, valid at the resonant frequency, is shown in FIG. 3(b). Here $C_T$ is the electrostatic capacitance and $G_a$ is the radiation conductance of the transducer. $C_T$ and $G_a$ can be calculated from the equations $$C_T = C_o N W \tag{1a}$$

$$G_a = (4K^2 N/\pi)\omega_o C_T, \tag{1b}$$

where N=number of finger pairs, W=aperture, $\omega_o = 2\pi f_o$, and the material constants for 128° Y-X LiNbO$_3$ are $C_o = 480$ pF/m and $K^2 = 4.8 \times 10^{-2}$. Using N=10, W=2800 μm and $f_o = 75 \times 10^6$, then $C_T = 13.5$ pF and $G_a = 3.9 \times 10^{-3}$ S. The total acoustic power radiated by IDT 11 is then given by $$P = v_1^2 G_a \tag{2}$$

where $v_1$ is the rms value of the voltage across the transducer. Since, from FIG. 3(a), greater power is incident on end absorber 15, its temperature should be greater than that of end absorber 17. Heat would flow by conduction from end absorber 15 towards end absorber 17. Thus the temperature of end absorber 17 would also lag that of end absorber 15 following application of power to the oscillator loop.

Figure 4:
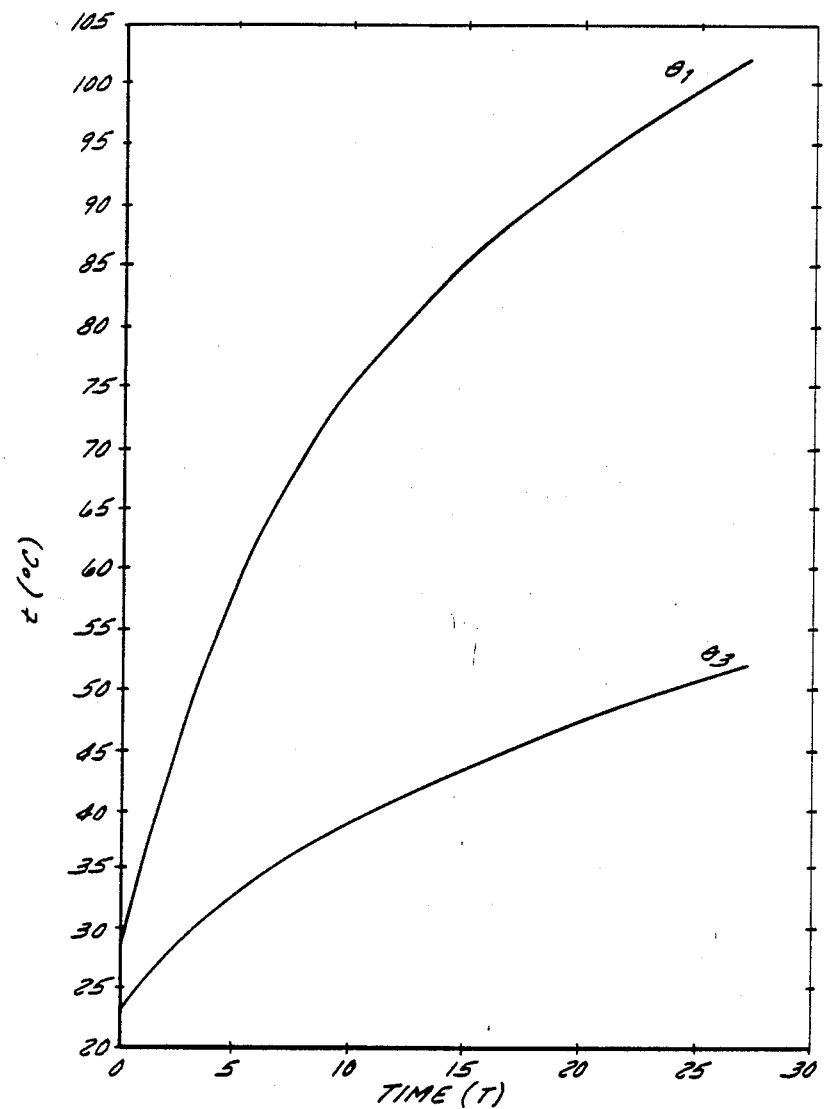
FIG. 4 shows the variation of substrate temperatures $\theta_1$ (input absorber) and $\theta_3$ (centerline edge) on a 128° Y-X LiNbO$_3$ delay line following application of ~150 mW RF power without gas flow.

FIG. 4 shows an example of experimentally observed variation with time of temperatures $\theta_1$ and $\theta_3$ measured by thermocouples TC$_1$ and TC$_3$ arranged as in FIG. 2. With no gas flowing through the test cell, heat was lost from the delay line by (a) conduction through the substrate to the mounting plate, (b) natural convection in the cell, and (c) conduction into the thermocouples and the leads connecting the delay line into the circuit. The power, P, radiated by the input transducer in this case was approximately 150 mW. Temperatures $\theta_1$ exceeding 100° C. can be attained. This is due to the small thermal mass of the SAW device. Both the initial lag of $\theta_3$ relative to $\theta_1$ and the sustained temperature difference of greater than 50° C. are evident in FIG. 4. These are due to the moderate thermal conductivity of LiNbO$_3$.

For use as a flow sensor, a large temperature gradient across the device may not be desirable but this example illustrates that a significant portion of energy present in he SAW can be efficiently converted to heat and that substantial temperature rise above ambient can be achieved because of the small thermal mass of the sensor.

Figure 5:
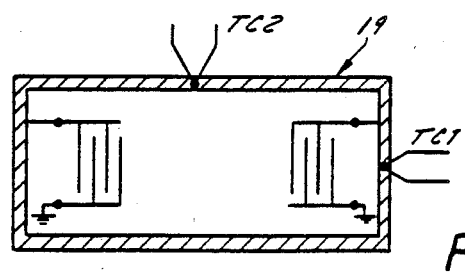
FIG. 5 is a schematic of a SAW delay line with end absorbers and a thermally conductive periphery.

It has been found that reasonably uniform substrate temperature can be achieved by using a thermally conductive material to form a closed thermal path 19 along the periphery of the device as shown in FIG. 5. With this arrangement, thermocouple measurement indicated that $(\theta_1 - \theta_2)$ was reduced to a steady-state value of less than 1° C. Of course, uniform substrate temperature can also be achieved by other transducer and/or absorber arrangements.

Figure 7:
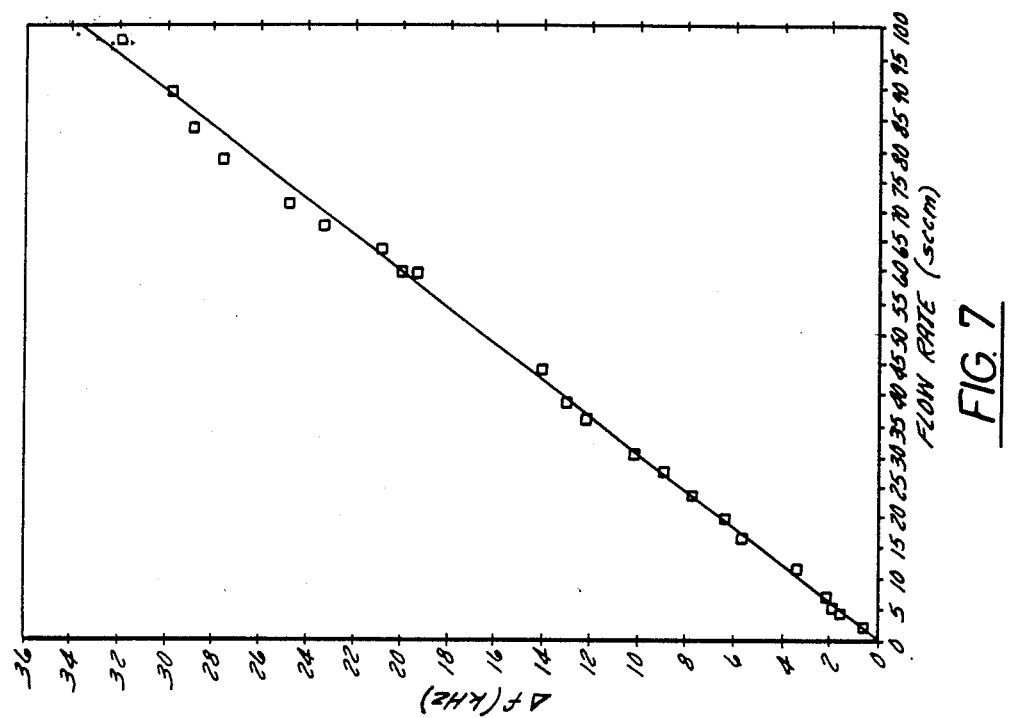
FIG. 7 shows low-flow response of the 75 MHz sensor.
Figure 6:
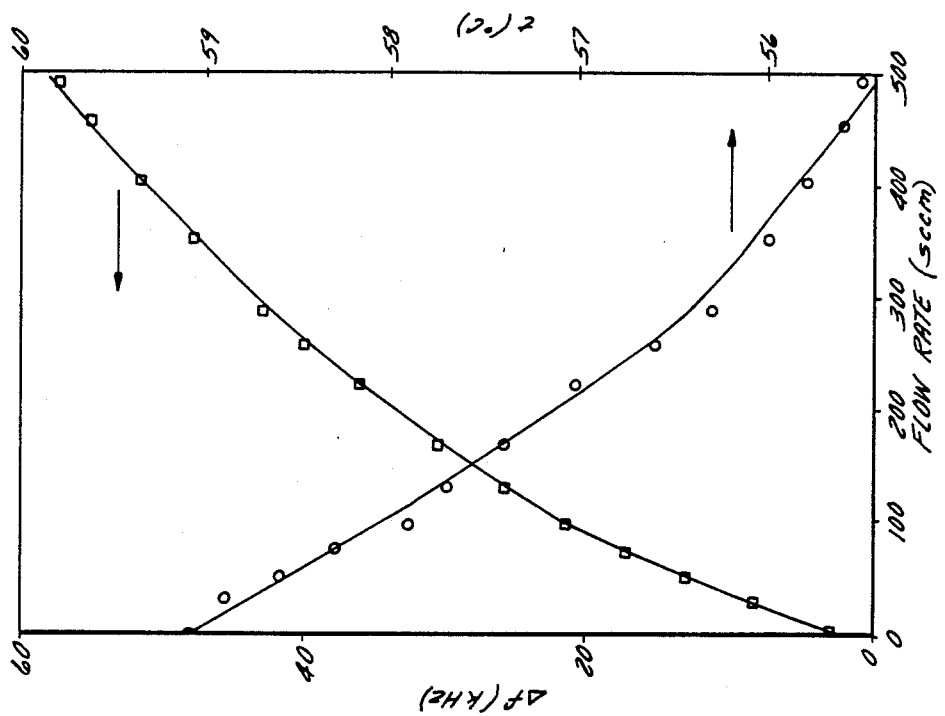
FIG. 6 shows the effect of gas flow rate on oscillator frequency and substrate temperature for a 75 MHz SAW flow sensor (structure as in FIG. 5).

The test cell containing the SAW device described above was connected to a source of dry nitrogen gas to study the performance of that device as a flow sensor. The cell was placed in series with a conventional mass-flow meter such as a Hastings-Raydist ST-500. The SAW oscillator was thermally configured as in FIG. 5 and its frequency was monitored as a function of flow rate. Measurements were carried out for various values of RF power in the oscillator loop. Results of one of these measurements are shown in FIG. 6. In this case the power in the oscillator loop was ~100 mW. With no gas flowing, the substrate temperature reached a value of 59° C. FIG. 6 shows the shift in oscillator frequency and the variation of substrate temperature θ as a function of flow rate. It is seen that oscillator frequency increases by more than 55 kHz as the flow rate varies from 0 to 500 standard cubic centimeters per second (sccm). In the range from 0 to 100 sccm, frequency varies almost linearly with flow rate. Data illustrating this are shown in FIG. 7. In this range, the frequency varies at the rate of 340 Hz/sccm. This corresponds to a fractional frequency change, Δf/f, of $4.67 \times 10^{-6}$ per sccm of flow. The resolution, which is defined as the smallest change in flow that can be detected, is limited by the short-term stability of the SAW oscillator. Laboratory measurements indicate oscillator stabilities better than 1 part in $10^6$. This implies a resolution of 0.2 sccm in this flow configuration.

Figure 8:
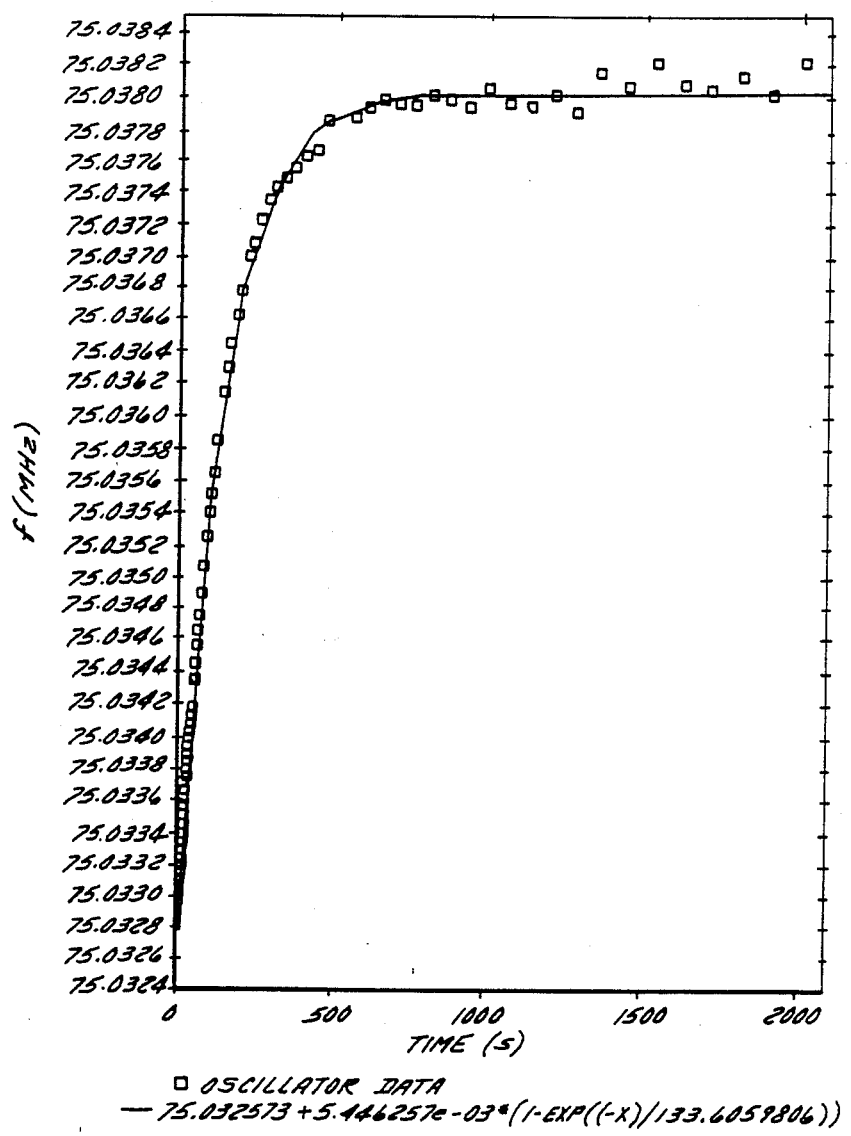
FIG. 8 shows the transient response of SAW sensor to a step increase in flow.

The response of the sensor to a step increase in flow rate is shown in FIG. 8. Here the flow rate was changed in nearly step fashion from 57 sccm to 235 sccm. The flow channel had a cross-sectional area of 0.97 cm$^2$, thus yielding average inlet velocities ranging from 0.98 cm/sec to 4.04 cm/sec for the step. The data are well approximated by a simple exponential function with a time constant of 134 s; this function is plotted as well on FIG. 8. There were similar temporal responses to step decreases in flow. The time constant can be improved by (a) increasing the thermal isolation of the delay line relative to its mount, (b) reducing the effective thermal mass, and (c) increasing the average gas velocity over the sensor surface.

To determine self-heating efficiency, a sensor with attached thermocouples, mounted in the aforementioned flow cell in a no-flow condition, was placed in an oscillator configuration with a broadband amplifier (ZHL-3A) and a 50Ω attenuator (H-P 335C). The RF voltage across the input IDT was monitored with an oscilloscope with a 1MΩ input impedance, the temperature $\theta_2$ at the centerline of the peripheral isothermal ring was measured by thermocouple, and the dc power applied to the amplifier was measured. The total acoustic power radiated by the input transducer was estimated from equation (2) with $G_a$ equal to 3.9 ms for this sensor. The following table shows the data for several power levels.

TABLE 1

| Amplifier | | RF Input | $\theta_2$ | P |
|---|---|---|---|---|
| ($V_{dc}$) | (mA) | ($V_{p-p}$) | (°C.) | (mW) |
| 12.2 | 30 | 2.2 | 21.9 | 2.4 |
| 15.0 | 60 | 4.9 | 23.5 | 11.7 |
| 17.0 | 90 | 6.0 | 26.4 | 17.6 |
| 22.3 | 170 | 13.8 | 47.5 | 92.6 |

The amplifier power levels are presented for documentation and are not related to self-heating efficiency or sensing characteristics. Ambient laboratory temperature was 20±1° C. It is apparent that considerable self-heating is achieved at modest input power levels for this device design. The (two) thermocouples attached for independent monitoring also function as heat sinks to reduce the operating temperature, and it is likely much higher average delay-line temperature were actually achieved than those measured at the periphery of the device. Thus, the data of Table 1 are illustrative of the minimum expected self-heating performance and not representative of that which would be typically obtained in the practice of this invention.

Devices such as those described above can also be constructed for chemical sensing applications. For these applications, a chemical coating is placed over the substrate in the propagation region. The chemical coating is selected for sensitivity to specific contaminants in the gas passing over the substrate. Thus, in the arrangement described above, a chemical coating selectively sensitive to particular contaminants can be used to detect the presence of the contaminants as the gas flows over the delay-line.

A SAW oscillator using a delay-line and end absorbers as described above can also be used to measure liquid flow using a back-side sensing technique. In back-side sensing, the back of the delay-line makes contact with the liquid flowing under it. The thickness of the substrate must be several times the acoustical wave length on the surface, as determined by the spacings of the interdigital transducers. Typically, the thickness of the substrate must be at least 5 to 10 times the acoustical wave length. The upper limit of the substrate thickness is limited only by the thermal conductivity characteristics of the substrate. In back-side sensing, the SAW delay-line structure described above is also coupled with an amplifier to form a stabilized oscillator. When a liquid flows across the back surface of the delay-line a change in frequency of the oscillator can be measured to determine the velocity of the fluid flowing under the delay-line.

The SAW delay line described above can also be used with a reference delay-line in mass flow sensing applications. In mass flow sensing, a first SAW delay line with end absorbers absorbs acoustical energy heating the first delay-line above a surrounding ambient temperature. The delay-line is coupled to an amplifier to form a stabilized oscillator with elevated delay-line temperature. A second or reference delay-line with substantially identical temperature coefficient of delay is coupled to an amplifier to form a stabilized oscillator with substantially ambient temperature operation. The delay-lines are then mounted with thermal isolation in a flow conduit of substantially fixed cross-sectional area and fluid is passed across the delay-lines. As a result of the self-heating affects in the first delay-line, the resonant frequency of both oscillators will be different. This difference in the resonant frequency of the oscillators can be used to determine the mass flow rate of the fluid. As previously discussed, gases are passed over the top of the substrate while liquid flow is measured with backside sensing techniques.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A surface acoustic wave delay line sensor comprising:
   (a) a planar piezoelectric substrate having first and second ends;
   (b) transmitting and receiving interdigital transducers disposed on a surface of the substrate and separated by a propagation region;
   (c) absorber means for heating the delay line above a surrounding ambient temperature, said absorber means further comprising:
      i a first acoustic end absorber disposed between the first substrate end and the transmitting transducer; and
      ii a second acoustic end absorber disposed between the second substrate end and the receiving transducer.

2. The device recited in claim 1 wherein the first and second acoustic end absorbers comprise thermally conductive material.

3. The device recited in claim 1 wherein the substrate has a temperature coefficient of delay of about $10^{-4}/°C$.

4. The device recited in claim 1 wherein the transducers have an operating frequency range from about 10 MHz to 1000 MHz.

5. The device recited in claim 1 wherein the transducers have a resonant frequency of about 75 Hz.

6. A device as recited in claim 1 wherein said substrate has a minimum thickness of between about five times and about ten times an acoustic wavelength of said delay line as determined by said interdigital transducers.

7. The device recited in claim 1 further comprising a chemically sensitive coating on the substrate in the propagation region.

8. A surface acoustic wave delay line sensor comprising:
   (a) a planar piezoelectric substrate having first and second ends;
   (b) transmitting and receiving interdigital transducers disposed on a surface of the substrate and separated by a propagation region;
   (c) a first acoustic end absorber disposed between the first substrate end and the transmitting transducer;
   (d) a second acoustic end absorber disposed between the second substrate end and the receiving transducer;
   (e) the first and second acoustic end absorbers absorbing mechanical and electrical energy components from the acoustic wave, thereby heating the delay line above a surrounding ambient temperature; and
   (f) means for distributing heat generated in the end absorbers around the substrate.

9. The device recited in claim 8 wherein the heat distribution means comprises a thermally conductive material disposed in a closed path around a periphery of the substrate.

10. A method of measuring a velocity of gas with a surface acoustical wave delay line having interdigital transmitting and receiving transducers separated by a propagation region of a substrate comprising the steps of:

(a) heating the delay line above a surrounding ambient temperature by absorbing acoustical energy in absorbers disposed between ends of the substrate and the interdigital transducers;

(b) coupling an amplifier with the delay line to form a stabilized oscillator with elevated delay-line temperature and passing a fluid across said delay-line and;

(c) measuring a resonant frequency of the oscillator and thereby determining the velocity of the gas from said resonant frequency.

11. The method of claim 10 further comprising providing a thermally conductive path around a periphery of the substrate.

12. The method of claim 10 wherein the step of passing a fluid across said delay line comprises passing a gas over a top side of said delay line.

13. The method of claim 10 wherein the step of passing a fluid across said delay line comprises passing a liquid across a bottom side of said delay line.

14. The method of claim 13 further comprising forming said substrate with a minimum thickness of between about five times and about ten times an acoustic wavelength of said delay line as determined by said interdigital transducers.

15. A method of monitoring selective contaminants in a gas with a surface acoustical wave delay line having interdigital transmitting and receiving transducers separated by a propagation region coated with a said contaminant sensitive coating on a top surface of a substrate comprising the steps of:

(a) passing a sample of the gas to be monitored across the contaminant sensitive coating on the top surface of the surface acoustical wave delay line (b) heating the delay line above a surrounding ambient temperature by absorbing energy in absorbers disposed between ends of the substrate and the interdigital transducers;

(c) coupling an amplifier with the delay line to form a stabilized oscillator;

(d) measuring a resonant frequency of the oscillator and determining the presence of said contaminants in the gas.

16. A method of mass flow sensing comprising the steps of:

(a) providing a first surface acoustical wave delay line with interdigital transmitting and receiving transducers separated by a propagation region on a surface of a substrate, the delay line also having acoustic end absorbers disposed between ends of the substrate and the interdigital transducers for absorbing acoustical energy and heating the delay line above a surrounding ambient temperature;

(b) coupling a first amplifier with said first delay line to form a first stabilized oscillator with elevated delay line temperature;

(c) providing a second delay line having a temperature coefficient of delay substantially equal to a temperature coefficient of delay of said first delay line;

(d) coupling a second amplifier with said second delay line to form a second stabilized oscillator, said second oscillator having substantially ambient temperature operation;

(e) providing a flow conduit of substantially fixed cross sectional area with mounting means and thermal isolation means for said delay lines;

(f) mounting said delay lines with said thermal isolation means and said mounting means to pass a fluid across said delay lines;

(g) measuring a resonant frequency of both said oscillators when said fluid is passed over the delay lines and computing a difference frequency;

(h) determining a mass flow rate from said difference frequency.

17. The method of claim 16 wherein the step of passing a fluid across said delay lines comprises passing a gas over a top side of said delay lines.

18. The method of claim 16 wherein the step of passing a fluid across said delay lines comprises passing a liquid across a bottom side of said delay lines.

19. A method of measuring a velocity of gas comprising the steps of:

(a) providing a surface acoustical wave delay line with interdigital transmitting and receiving transducers separated by a propagation region on a surface of a substrate;

(b) heating the delay line with acoustic end absorbers, disposed between ends of the substrate and the interdigital transducers, said end absorbers absorbing acoustical energy and heating the delay line above a surrounding ambient temperature;

(c) coupling an amplifier with the delay line to form a stabilized oscillator with elevated delay-line temperature and passing a fluid across said delay-line; and (d) measuring a resonant frequency of the oscillator and thereby determining the velocity of the gas from said resonant frequency.

* * * * *